US009296298B2

(12) United States Patent
Williams et al.

(10) Patent No.: US 9,296,298 B2
(45) Date of Patent: Mar. 29, 2016

(54) ALCOHOL DETECTION SYSTEM FOR VEHICLE DRIVER TESTING WITH INTEGRAL TEMPERATURE COMPENSATION

(71) Applicant: Transbiotec, Inc., Seal Beach, CA (US)

(72) Inventors: Nolann George Williams, Fallbrook, CA (US); Ronald Louis Williams, Fallbrook, CA (US)

(73) Assignee: Transbiotec, Inc., Seal Beach, CA (US)

( * ) Notice: Subject to any disclaimer, the term of this patent is extended or adjusted under 35 U.S.C. 154(b) by 0 days.

(21) Appl. No.: 14/564,575

(22) Filed: Dec. 9, 2014

(65) Prior Publication Data

US 2015/0165903 A1 Jun. 18, 2015

Related U.S. Application Data

(63) Continuation-in-part of application No. 13/417,595, filed on Mar. 12, 2012.

(51) Int. Cl.
| | |
|---|---|
| *G01N 33/48* | (2006.01) |
| *G01N 33/49* | (2006.01) |
| *B60K 28/06* | (2006.01) |
| *B60N 2/00* | (2006.01) |
| *G01N 27/04* | (2006.01) |
| *G01N 27/14* | (2006.01) |
| *G01N 33/98* | (2006.01) |
| *A61B 5/18* | (2006.01) |
| *G01N 33/483* | (2006.01) |

(Continued)

(52) U.S. Cl.
CPC ............. *B60K 28/063* (2013.01); *B60K 28/06* (2013.01); *B60N 2/002* (2013.01); *G01N 33/4833* (2013.01); *G01N 33/4972* (2013.01); *A61B 5/18* (2013.01); *B60W 2040/0836* (2013.01); *B60W 2540/24* (2013.01); *G01N 27/04* (2013.01); *G01N 27/14* (2013.01); *G01N 33/98* (2013.01); *Y10S 436/90* (2013.01)

(58) Field of Classification Search
CPC ................... B60K 28/063; B60W 2040/0836; G01N 33/98; A61B 5/18; Y10S 436/90
See application file for complete search history.

(56) References Cited

U.S. PATENT DOCUMENTS

| | | | | |
|---|---|---|---|---|
| 4,738,333 | A * | 4/1988 | Collier et al. | 180/272 |
| 4,749,553 | A * | 6/1988 | Lopez et al. | 422/84 |
| 5,020,628 | A * | 6/1991 | Bigliardi et al. | 180/272 |

(Continued)

OTHER PUBLICATIONS

Figaro, General Information for TGS Sensors, Mar. 2005, retrieved from http://www.figarosensor.com/products/common(1104).pdf.*

*Primary Examiner* — Mussa A Shaawat
*Assistant Examiner* — Thomas Ingram
(74) *Attorney, Agent, or Firm* — Felix L. Fischer (57) ABSTRACT

An alcohol detection system incorporates a resistive touch sensor mountable in a vehicle for determining presence of alcohol based on changed skin resistance. An ignition interlock is provided in the vehicle and a microcontroller is connected to and receives data from the touch sensor and provides a signal to open the interlock to disable the vehicle upon receipt of data from the touch sensor exceeding a predetermined value. The system also employs operator identification and vehicle location systems with a data logger allowing the microcontroller to store data on test results, operator identification and vehicle location. Additionally, the system may employ a cellular communication system to allow reporting of the data to a remote location.

20 Claims, 9 Drawing Sheets

(51) Int. Cl.
*G01N 33/497* (2006.01)
*B60W 40/08* (2012.01)

(56) References Cited

U.S. PATENT DOCUMENTS

| | | | |
|---|---|---|---|
| 5,426,415 A * | 6/1995 | Prachar et al. | 340/576 |
| 5,944,661 A * | 8/1999 | Swette et al. | 600/345 |
| 6,229,908 B1 * | 5/2001 | Edmonds et al. | 382/124 |
| 6,620,108 B2 * | 9/2003 | Duval et al. | 600/532 |
| 2002/0127145 A1 * | 9/2002 | Der Ghazarian et al. | 422/83 |
| 2003/0183437 A1 * | 10/2003 | Mendoza | 180/272 |
| 2005/0241871 A1 * | 11/2005 | Stewart et al. | 180/272 |
| 2007/0144812 A1 * | 6/2007 | Stewart et al. | 180/272 |
| 2008/0316037 A1 * | 12/2008 | Shoji et al. | 340/576 |
| 2011/0015873 A1 * | 1/2011 | Iiams et al. | 702/24 |
| 2011/0050407 A1 * | 3/2011 | Schoenfeld et al. | 340/426.11 |

* cited by examiner

FIG. 6B

ALCOHOL DETECTION SYSTEM FOR VEHICLE DRIVER TESTING WITH INTEGRAL TEMPERATURE COMPENSATION

REFERENCE TO RELATED APPLICATIONS

This application is a continuation-in-part of U.S. application Ser. No. 13/417,595 filed on Mar. 12, 2012 entitled ALCOHOL DETECTION SYSTEM FOR VEHICLE DRIVER TESTING and a common assignee, the disclosure of which is incorporated herein by reference.

BACKGROUND INFORMATION

1. Field

Embodiments of the disclosure relate generally to the field of alcohol detection systems and more particularly to a skin resistive sensor detection system incorporating ignition interlock capability, reporting, operator identification and vehicle location systems.

2. Background

The detection of alcohol impairment has long been a significant issue for operators of motor vehicles. Accidents and fatalities due to driving while under the influence of alcohol continue to increase and even with strong enforcement of vehicle codes imposing significant fines and sentencing of offenders, passive deterrence remains ineffective for reducing the incidences of driving while impaired.

For operators of commercial vehicles the potential liabilities associated with drivers operating vehicles while impaired by alcohol have significant economic impact. Consequently, real time testing of vehicle operators and the capability to identify and confirm the tested individual to assure that the driver of the vehicle is the individual taking the test is desirable.

Prior art systems for alcohol detection/testing in vehicular applications typically employ breath or vehicle interior gas detection for alcohol vapor. Systems for alternative detection forms have been costly and most systems are complex and/or excessively expensive or do not provide desired reliability in detection.

It is therefore desirable to provide an alcohol detection system for vehicle driver testing which employs reduced complexity while providing precise detection capability. It is further desirable for the system to provide identification of the tested driver to assure that the tested individual is the vehicle operator. It is also desirable for the system to provide affirmative vehicle disablement or identification with automated communication of status.

SUMMARY

Embodiments disclosed herein provide an alcohol detection system which incorporates a resistive touch sensor mountable in a vehicle with a vapor sensor for determining presence of alcohol based on changed resistance in a predetermined interval. An ignition interlock is provided in the vehicle and a microcontroller is connected to and receives data from the touch sensor and provides a signal to open the interlock to disable the vehicle upon receipt of data from the touch sensor exceeding a predetermined value, or alternatively with the interlock initially open to prevent operation of the vehicle, closing the interlock to allow operation of the vehicle upon passing of the test.

In certain embodiments, the system also employs operator identification and vehicle location systems with a data logger allowing the microcontroller to store data on test results, operator identification and vehicle location. Additionally, the system may employ a cellular communication system to allow reporting of the data to a remote location.

The embodiments disclosed provide a method for disabling a vehicle with an alcohol detection system including a resistive touch sensor where when the system is powered on a startup time is recorded on a data logger by a microcontroller. An operator indicator to is then activated to notify an operator that a test is required at a predetermined time programmed into the microcontroller. The touch sensor data is then read when the operator places a finger on the touch sensor and a second operator indicator is activated signifying that the test is in process. The elements of an identity verification system and location and anti-theft system are also activated. Data is then collected with the microcontroller from the touch sensor, identity verification system and the location and antitheft system. If the operator removes his finger before testing is complete, the microcontroller returns to the step of activating the operator indicator a requiring the operator to restart the test, otherwise, the second operator indicator is extinguished notifying the operator that the test is complete. Time/date information and data from the touch sensor, identity verification system and location and anti-theft system are then stored in a data logger. If the test result shows impairment, operator is notified with a third operator indicator to show test failure and the ignition interlock is opened preventing operation of the vehicle. If no impairment is shown by the test, the microcontroller remains inactive for a predetermined period until additional testing is required.

The features, functions, and advantages that have been discussed can be achieved independently in various embodiments of the present disclosure or may be combined in yet other embodiments further details of which can be seen with reference to the following description and drawings.

DETAILED DESCRIPTION

Embodiments disclosed herein provide an alcohol detection system incorporating a hand held or mountable detector case with a resistive touch sensor and vapor sensor to measure a finger of a test subject such as a vehicle operator, a microprocessor control system with data recording and communications capability, a vehicle systems interface, an identity verification system and a location confirmation system.

Figure 1A:
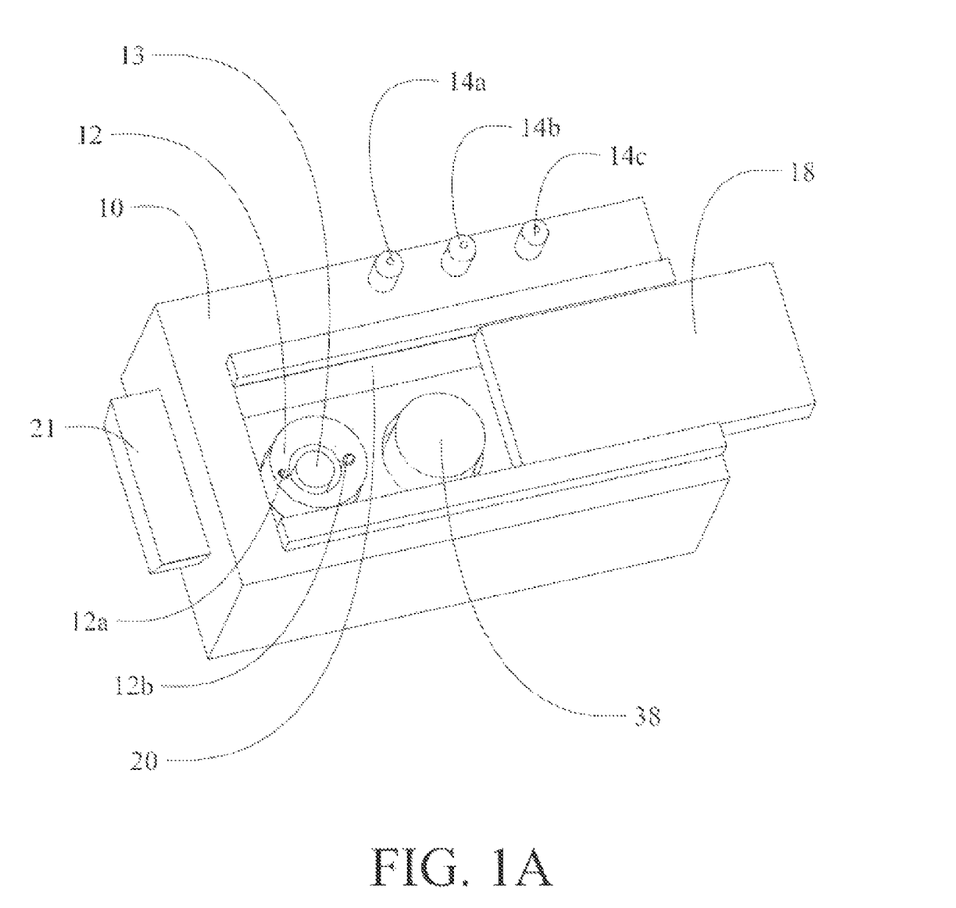
FIG. 1A is pictorial view of an exemplary sensor subassembly to be employed with embodiments of the invention.
Figure 1B:
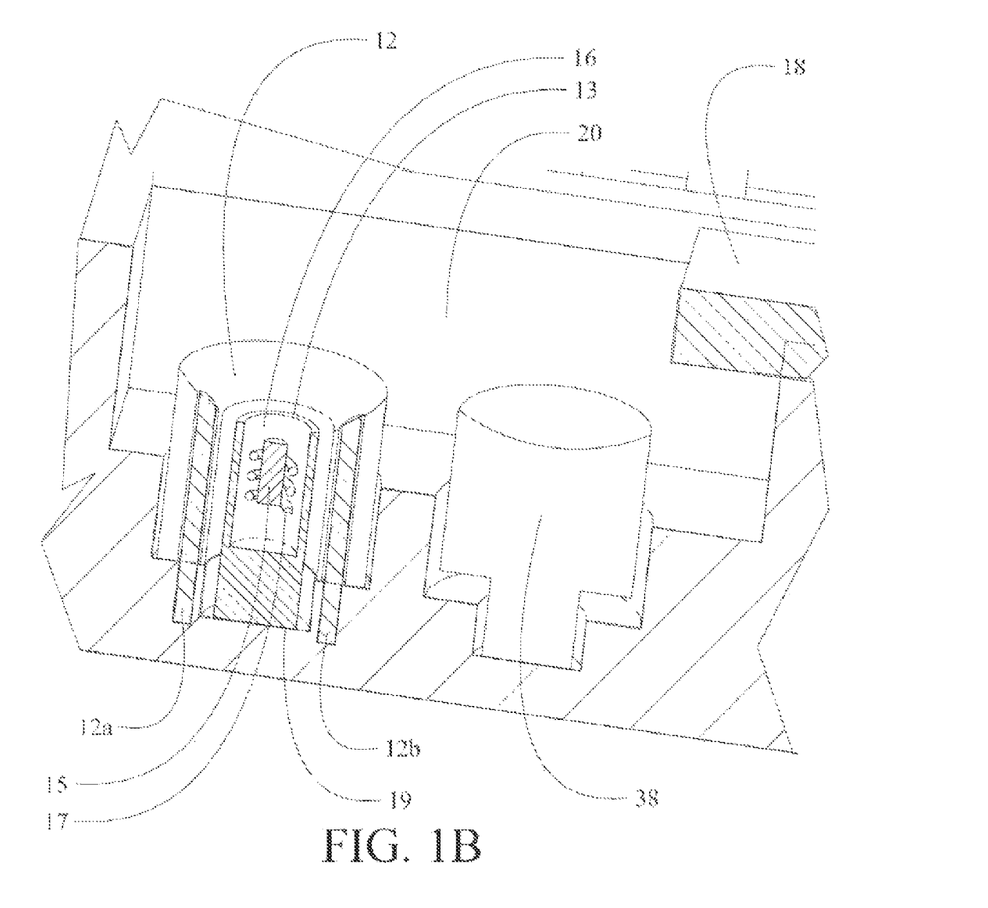
FIG. 1B is a partial side section view of details of the sensor subassembly of FIG. 1A.

Referring to FIGS. 1A and 1B, a detector case 10 houses a resistive touch sensor, generally designated as element 12, and an ethanol vapor sensor 13. The touch sensor incorporates a plastic housing with two wire probes 12a and 12b (best seen in FIG. 1B) which are exposed at a surface around the cavity 16 surrounding the vapor sensor 13 as a gas sensing volume. The touch sensor measures skin resistance and only triggers for sampling the vapor sensor if the resistance shown is between about 100 kilohms and 1.5 megaohms. A lower resistance and the vapor sensor is inoperative thus a conductive covering on the finger of the test subject such as aluminum foil cannot be used to fool the detector. A higher resistance equally renders the touch sensor inoperative so a rubber glove covering the finger of the test subject also cannot be used to fool the detector.

For an example embodiment, the vapor sensor is a tin oxide-Taguchi type sensor. Vapor sensors suitable for initial embodiments have been identified as available from Figaro Engineering Inc. 1-5-11 Senba-nishi Mino, Osaka 562-8505 JAPAN. The Taguchi sensor incorporates a tin oxide coated ceramic element 15 and a heater screen printed on its surface, represented by helix 17. The vapor sensor is suspended inside a standard TO-5 package 19 with a stainless steel screen over the top (not shown in the drawings for clarity) to provide a sampling volume shown as cavity 16. The tin oxide is selective to the gas it is most sensitive to based on its temperature. The tin oxide sensor changes its resistance as a function of ethanol gas concentration. A change in resistance greater than ~1 k+ ohms to indicates enough alcohol in body to indicate operator impaired performance of vehicle operation.

Tin oxide vapor sensors are temperature dependent for maximizing sensitivity to various detectable vapors. At about 440 C detection of ethanol is optimum. The most common Taguchi sensor application is in refineries where the sensor is heated to about 540 C and is most sensitive to hydrogen sulfide. The heater element is sized differently to produce a range of sensors with most selective response to a specific gas. If the tin oxide sensor is at any other temperature than its set point it is less sensitive to ethanol and more sensitive to other gases. Since the ambient temperature affects the case temperature and this case temperature affects the sensor element, the most sensitive reading is only when the sensor is at its set point which has been calibrated at an ambient temperature of approximately 20 C. To compensate for ambient temperature differential, at typical ambient temperature variation ranges, the vapor sensor cannot just measure resistance as a function of ethanol vapor concentration since the variation of tin oxide resistance due to ambient temperature variation is greater than the variation produced by a normal and an excessive alcohol value. For this reason the detector for the embodiments disclosed triggers on an initial and second subsequent resistance reading to obtain a difference measurement after a sufficient predetermined time period for accumulation of gas in the sampling volume. For the embodiment disclosed herein, a resistance value is recorded as soon as the finger is first presented to the touch sensor, and then again after 6 seconds and uses the difference between the two readings to determine acceptance/rejection as will be described in greater detail subsequently.

Operator indicators 14 such as light emitting diodes (LEDs) 14a, 14b and 14c, the operation of which will be described in greater detail subsequently, are mounted in the detector case for communication of status and operational requirements of the system. In alternative embodiments, audible signaling may be used as a substitute for or in conjunction with the visual indicators. For the embodiment shown, the touch sensor 12 is mounted in a chamber 20 in the case allowing a slideable cover 18 to be placed over the touch sensor when not in use. Wiring for interconnection of the detector case to vehicle system is accomplished through plug 21 (actual wiring is omitted for clarity in the drawings).

Figure 2:
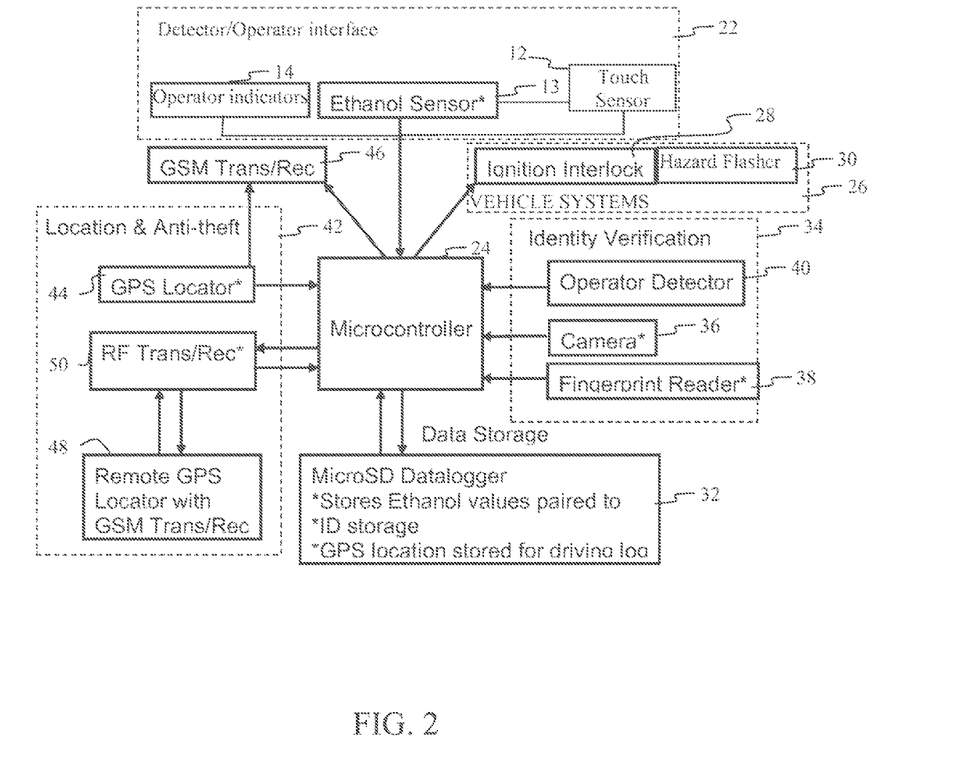
FIG. 2 is a block diagram of system elements for an embodiment.

As shown in FIG. 2, the touch sensor 12 and operator indicators 14 (LEDs 14a, 14b and 14c of FIG. 1) which constitute the operator/detector interface 22 are connected to a microcontroller 24 such as a model PIC16F870 (or 16F886)-/SO available from Microchip Technology Inc.

The microcontroller 24 receives signals from the touch sensor 12 and vapor sensor 13 and provides timing and control output to the operator indicators 14. The microcontroller 24 is also interconnected to applicable vehicle systems 26 including an ignition interlock 28 and, in certain embodiments, emergency flasher indicators 30. While shown in the embodiment in the drawings as a separate detector case 10, the operator/detector interface 22 may be integrated into the vehicle instrument panel or console. For the tin oxide Taguchi type sensor, the vapor sensor 13 is connected directly to the +12 V power system 27 of the vehicle to allow proper power and to maintain an "on" condition since the Taguchi type sensor requires a warm-up time for proper operation.

The microcontroller 24 receives data through an analog to digital converter 25 from the touch sensor 12 and vapor sensor 13 and provides output to the operator indicators 14 to require the initiation of a test and indicate test pass or fail. The microcontroller is programmed to test change in tin oxide vapor sensor resistance. When an operator's finger is touched to the touch sensor 12 in the detector case 10, if proper resistance is present across the wires 12a and 12b of the touch sensor, the vapor sensor 13 is activated. An initial resistance reading is taken by the microcontroller immediately upon activation and a second resistance reading is taken after a predetermined time differential. For the embodiment disclosed, the predetermined time differential is 6 seconds. A change in resistance of greater than ~1 k+ ohms between the initial resistance reading the second resistance reading indicates enough alcohol in body to indicate impaired operator performance with respect to vehicle operation. The operator indicators 14 provide notification to the operator that a test is required, whether the test has been completed properly and whether the test was passed or failed, as will be described in greater detail subsequently.

A data logger 32 is connected to the microcontroller for recording of test times and results. For an example embodiment, the data logger employs MicroSD cards for data storage. The microcontroller 24 and data logger 32 may be contained within the detector case 10 in certain embodiments. However, these elements of the system may be contained in a separate enclosure or integrated in the vehicle panel or consoles.

As previously described, the microcontroller 24 is interconnected to the ignition interlock 28 in the vehicle. Upon failure of a test, the microcontroller disables (or alternatively doe not enable) the ignition of the vehicle preventing the vehicle from being driven. For an example embodiment, the ignition interlock will have a zener diode overvoltage suppression system 29 and series diodes for protecting microcontroller circuitry. Twisted/shielded wiring is employed to further shield the microcontroller from spurious noise radiated from vehicle environment. For an example embodiment, the touch sensor employs an internal relay rated for 1 AMP maximum contact current which is derated to ¼amp for an automobile application. Most switching circuitry in a vehicle requires 2-4 amps peak current during contact/FET break. The switched interlock line incorporates a point of use relay with standard diodes across the contacts to inhibit contact pitting, a zener diode across the energizing circuit from the touch sensor relay and a series diode from the positive relay line to the point of use relay to suppress EMI and protect the microcontroller. In alternative embodiments, the microcontroller may also engage the vehicle hazard flasher 30 for external identification.

An identity verification system 34 is also interfaced to the microcontroller 24. A still or video camera 36 is employed as a portion of the identity verification system to record an image of the actual vehicle operator. The field of view of the camera may include the face as well as the arm and had of the operator to confirm that operator's hand is, in fact, placed on the touch sensor 12. In addition, or alternatively, a fingerprint reader 38 as shown in FIGS. 1A and 1B may be employed as a portion of the identity verification system. Returning to FIG. 2, an operator detector 40 confirms the presence of the operator in the driver's seat of the vehicle. All data from the identity verification system elements is provided by the microcontroller 24 to the data logger 32 which, for the exemplary embodiment, configures received serial data into an FAT16 data structure and stores it on the MicroSD cards in the data logger 32, also allowing retrieval of stored data to interfaced systems. Data can be stored from any microcontroller interfaced sensor system, such as time, temperature, pictures, or other integrated peripherals. This allows the company operating the vehicle or factory to determine long term calibration issues and sensor calibration times by trending. Additionally the data is useful for company supervision to verify the alcohol detection system was working as designed in case of positive test results. As an added benefit, when using the camera or fingerprint reader elements of the identity verification system, the recorded data will certify that the operator was operating his vehicle according to federal requirements for time behind the wheel.

The fingerprint reader 38 allows biometric recording of operation and testing. In the example embodiment, the fingerprint reader 38 is placed in a location adjacent to the touch sensor 12 as shown in FIGS. 1A and 1B thus requiring two finger operation, with an index finger placed on the touch sensor and the adjacent middle finger placed on the fingerprint reader, further guaranteeing that the operator who is taking the test is the correct person. In alternative embodiments, the alcohol sensor may be integrated into the biometric fingerprint reader.

In an exemplary embodiment, the operator detector 40 employs the operator seated in the seat as an antenna for a ~900 khz signal generated by a wire coil 41 under the seat. When the alcohol detection system is energized, the wire coil under the sear is energized by a ~900 khz signal. An electronic filter associated with the touch sensor inputs only accepts the ~900 khz signal as an initiator for the testing A location and antitheft system 42 incorporates a global positioning system (GPS) locator 44 interfaced to the microcontroller 24. This allows realtime actual location of the vehicle to be recorded by the microcontroller 24 in the data logger 32. A global system for modular communications (GSM) transmitter receiver 46 may be interfaced to the microcontroller 24 and or GPS locator 44 for transmission of the realtime position to a remote facility for monitoring of vehicle location. The microcontroller may also transmit test results, driver identification or other data through the GSM transmitter/receiver to the remote facility. For the example embodiment, the GSM transmitter/receiver employs the existing cellular phone infrastructure, allowing packets of data to be sent/received from the remote facility or another system integrated to the cellular phone infrastructure. This allows for transmission by the microcontroller of testing results, and other applicable data, such as position, video, sound and other information available from any elements of the system. Further, the GSM transmitter/receiver also allows for system software modification for the microcontroller for upgrades and real-time control of all attached hardware, including managerial overrides to system failures.

The location and antitheft system 42 may also employ a remote GPS locator 48 which is wirelessly interfaced to the microcontroller 24 through an RF transmitter/receiver 50 or other known wireless interface. The RF transmitter/receiver 50 also allows transmission of signals for communications between the microcontroller and any other nearby RF capable systems as an alternative to the GSM transmitter/receiver 46. This allows microcontroller interface for purposes of storage or transmission of data from other nearby RF capable systems even if cellular service may not be available. The remote GPS locator 48 may be a combined small GPS/cell phone transmitter with independent power supply capable of autonomously transmitting information. Modern anti-theft devices allow location of automobiles/trucks. However, such systems have several disadvantages since generally their location is confined to a limited area adjacent to the automotive power supply and as such are easily traceable. The remote GPS locator 48 as an independent system with internal battery power receiving negative feedback, for example via wireless transmission, from other systems and may remain passive (and on low power) until removal of such feedback (such as car theft) or external stimuli such as unauthorized movement, then activate and allow tracking of the automobile to its destination. Placement could easily be literally anywhere in the automobile/truck, battery endurance would be 1-2 years and size approximately the same as a cigarette package.

Figure 3:
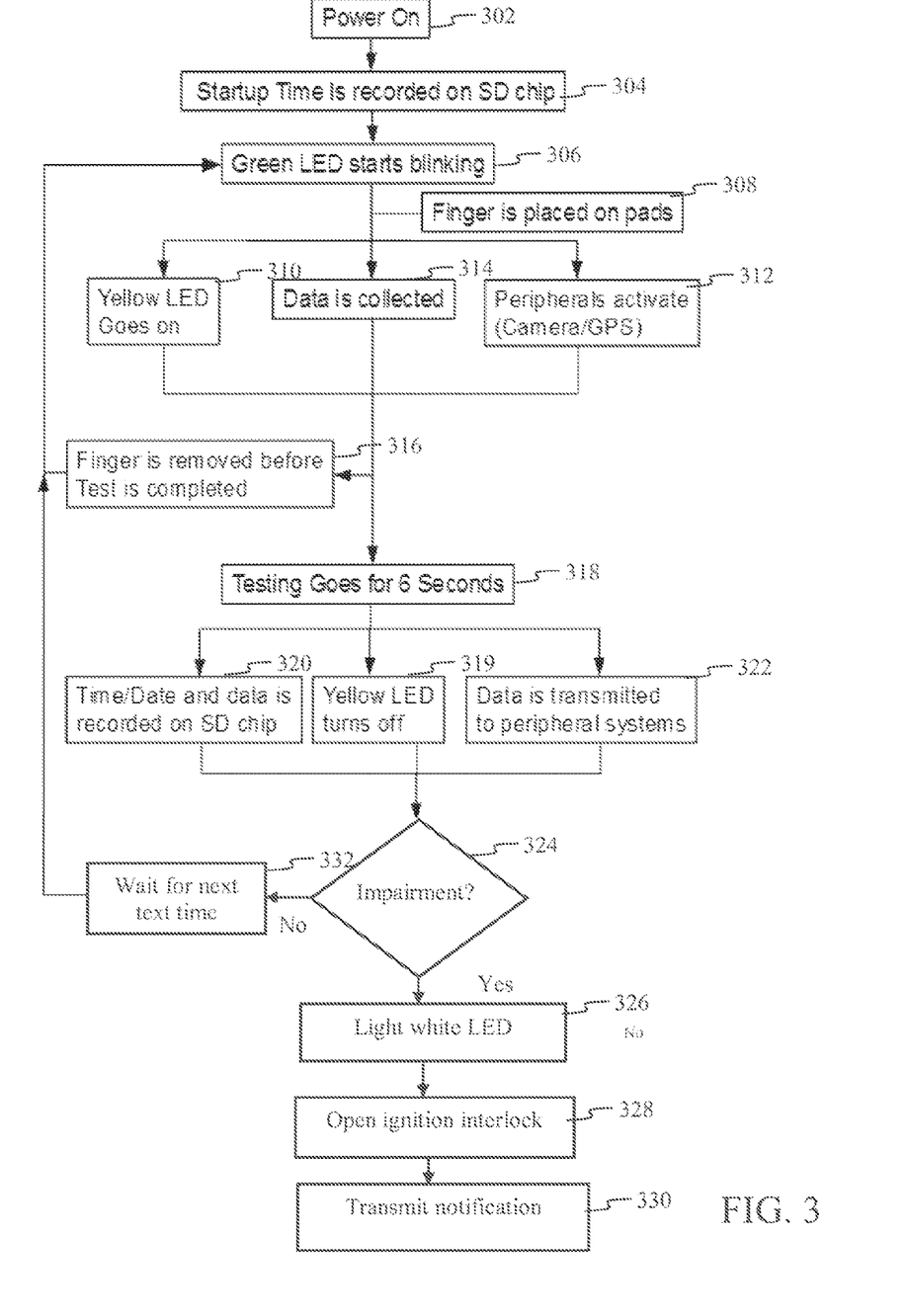
FIG. 3 is a flow chart of system operation.
Figure 4:
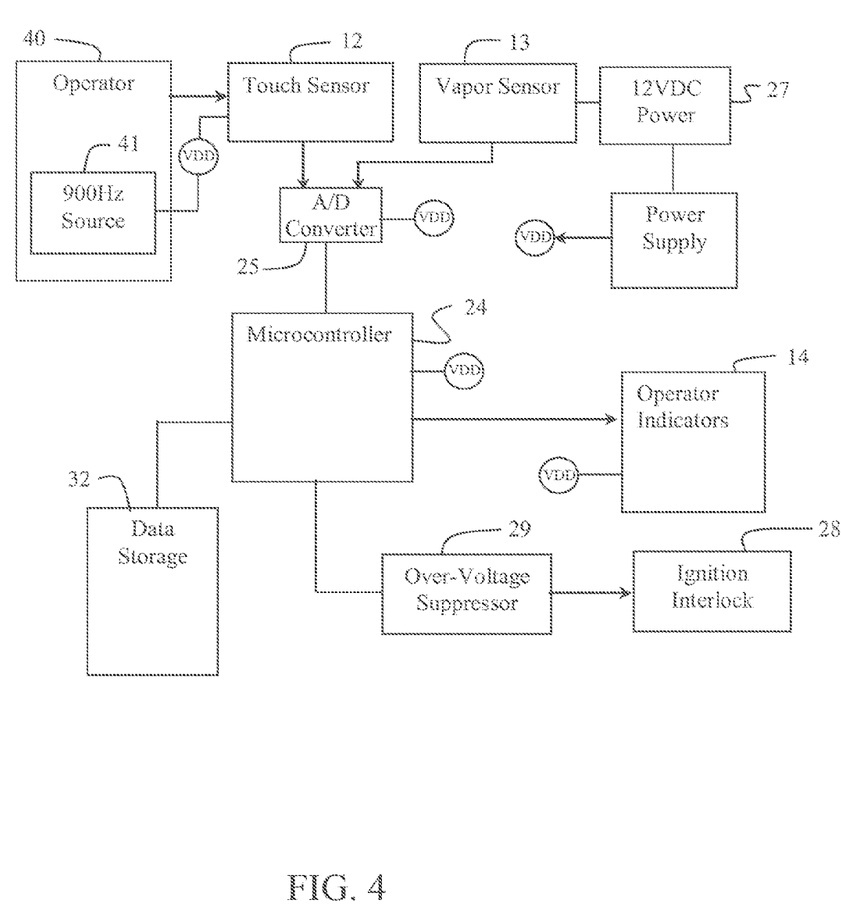
FIG. 4 is a schematic of example electrical circuit elements of the embodiment.

Operation of the alcohol detection system as defined in the described embodiments is shown in FIG. 3. The system is powered on, step 302, and a startup time is recorded on the data logger by the microcontroller 24 step 304. At a predetermined time programmed into the microcontroller 24 (which may be at startup or another time as appropriate), the microcontroller activates the operator indicators 14 to notify the operator that a test is required. For the example embodiment, indicator LED 14a which is a green LED is caused to blink, step 306. The operator then places a finger on the touch sensor 12 and vapor sensor 13 (and on the fingerprint reader 38 if so equipped for operator identification) for data to be read by the microcontroller, step 308. The microcontroller activates a second operator indicator, which for the embodiment shown is LED 14b, a yellow LED, signifying that the test is in process, step 310. The microprocessor 24 activates the elements of the identity verification system 34 and location and anti-theft system 42, step 312. Data is collected by the microcontroller 24 from the vapor sensor 13 with an initial reading and second reading at a predetermined time differential (6 seconds as previously noted for the present embodiment), identity verification system 34 (including fingerprint reader, camera and operator detector) and the location and antitheft system 42 including GPS location, step 314. If the operator removes his finger(s) before testing is complete (before the second reading at the predetermined time differential), step 316, the microprocessor returns to step 306 reactivating the green LED 14a requiring the operator to restart the test. When testing is completed, step 318 (approximately 6 seconds for the disclosed embodiment), the microprocessor extinguishes the yellow LED 14b notifying the operator that the test is complete, step 319. Time/date information and data from the vapor sensor, identity verification system and location and anti-theft system are stored by the microcontroller in the data logger, step 320. The microcontroller may transmit the stored data to a remote facility by employing the GSM Transmitter/receiver 46 or the RF transmitter receiver 50, step 322. If the test result shows impairment, step 324, the microcontroller provides notification to the operator via a third operator indicator, in the embodiment LED 14c which is a red LED, which illuminates to show test failure, step 326. The microcontroller then opens the ignition interlock 28 preventing operation of the vehicle and/or illuminates the vehicle hazard flasher 30, step 328. If programmed to do so, the microcontroller may additionally notify the company or other authorities by transmitting data using the GSM transmitter/receiver with test result data, vehicle location from the GPS locator and driver identification from the identity verification system, step 330.

If no impairment is shown by the test, the microcontroller then remains inactive for a predetermined period until additional testing is required, step 332.

Data transmitted may be employed not only for confirmation of no driver alcohol impairment but may also provide records for federal, state or company driver log requirements. In an example operational scenario, the biometric fingerprint data and/or recorded camera images and rolling retest logic will identify the operator and record his presence behind the wheel. The notification may be by the GSM transmitter receiver as cell phone data or by interrogating the logged data recorded on the internal Mini SD data logger to prove after the fact compliance.

As previously noted, the tin oxide ethanol sensor is highly temperature sensitive. Increasing the accuracy of all tin oxide sensors by using one of the internal sensor elements in an electronic feedback loop as a calibration source assures that the sensor operates in an optimum sensitivity condition regardless of ambient temperature conditions. This method is only applicable to those applications which utilize gas sampling techniques. Tin oxide sensors are used in both continuous and gas sampling applications.

Prior art devices as disclosed by Figaro Corp of Japan on their website employ a similar calibration method using an external thermistor as a temperature sensor. Ambient temperature as read by the thermistor is provided as feedback to fine tune the sensor heater current so the sensor performs at a set temperature. Since the entire sensor element is less than 1 mm square this feedback method is a crude temperature compensation and slight air currents will still interfere with the sensor calibration.

Figaro type tin oxide sensors consist of a fixed heater element underneath a tin oxide sensor element. The tin oxide sensor has very high gas selectivity response based on the operating temperature. Thus many types of sensors which only differ in the heating element setpoint allows sensing selective for a specific gas. Even though the tin oxide sensor elements operate at hundreds of degrees C. the accuracy of the reading is strongly and quickly influenced by ambient air temperature.

The problem with the prior art is that the thermistor cannot be co-located with the sensing element and the sense element is very temperature dependent. Baseline readings can change 1000 ohms with as little as 2 degrees F. ambient temperature change or even slight air currents removing heat from the outer package surface. Tin oxide gas vapor sensors, also known as stannous oxide sensors, are designed to work optimally for specific gas detection at a fixed heater temperature in a 68 degree F. ambient environment.

In a first embodiment, the calibration resistance of the sensor element is employed to drive a feedback adjustment to the current of the internal heater so that the calibration is maintained over a wide ambient temperature range. This assures that the sensor is optimized for the preset gas detection. When the sensor is read the last control voltage for the sensor is captured and the heater current is frozen by a sample and hold technique when a gas sample is introduced for reading. Either an analog sample and hold or pulse width modulated (PWM) digital signal may be provided for control of the heater current to maintain a stable sensor temperature.

Figure 5A:
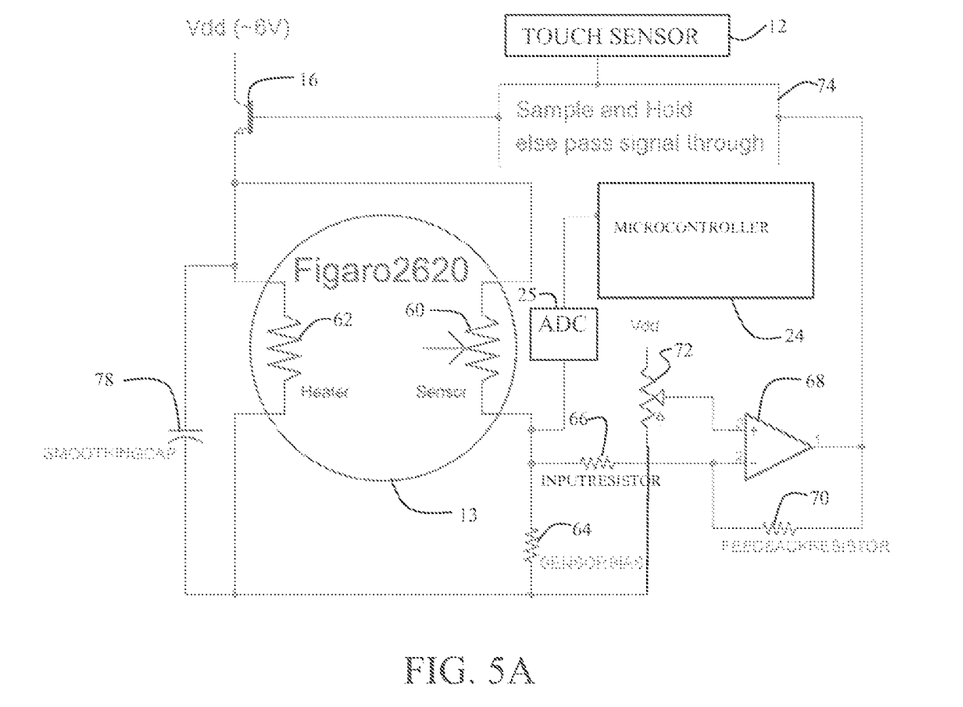
FIG. 5A is a schematic of a vapor sensor employing the sensor element for temperature compensation.

As shown in FIG. 5A, the vapor sensor 13 incorporates as internal components a sensor element 60 and an internal heater 62. An output of the sensor element is provided to the microcontroller 24 for ethanol sensing as previously described. Additionally, however, the sensor element 60 is connected between the sensor element and a sensor bias resistor 64 through an input resistor 66 to an operational amplifier 68 stabilized by a feedback resistor 70 and having calibration available through a rheostat 72 connected to the power source, Vdd. Output of the operational amplifier 68 is provided through a sample and hold circuit 74 which is activated by the touch circuit 12, previously described. A control transistor 76 between the power source, Vdd, and the vapor sensor 13 is gated by the sample and hold circuit 74 which freezes the supplied power at a current value when the touch sensor 12 is activated, thus holding current to the heater 62 at a fixed value during sensing of the sensor element 60. A smoothing capacitor 78 is employed in parallel with the heater 62.

Figure 5B:
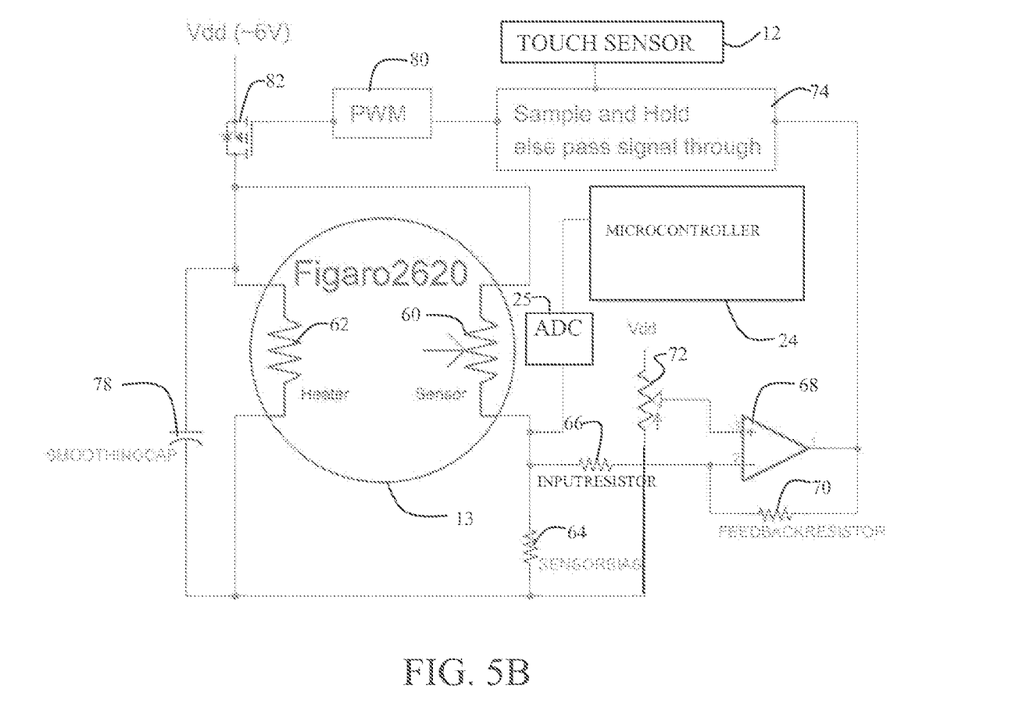
FIG. 5B is a schematic of a vapor sensor employing the sensor element for temperature compensation with pulse width modulation control.

Similar feedback control may be employed using PWM as shown in FIG. 5B wherein output form the sample and hold circuit 74 is provided to a PWM generator 80 which provides RMS averaging to a gating switch 82 between the power source, Vdd, and the vapor sensor 13.

Alternatively, the heater element in the vapor sensor may be employed for immediate local temperature sensing. The resistance of the heater element is proportional to its temperature according to $$R = R_0(1 + \alpha(T - T_0))$$

The proportional relationship makes the heater element a crude temperature sensor of sorts as resistance in the heater increases with temperature and decreases as temperature drops. This may be used in a feedback circuit to control and stabilize the temperature of the vapor sensor as a whole, preferably through use of a high temperature/resistance coefficient heater such as copper, though use of nichrome, the heater element of choice due to a low temperature/resistance coefficient should still suffice. In this way under V=IR, if both I and V are known the resistance of the heater element can be computed. The current through the heater can be determined by computing the current through a series resistor of known value using Ohms law and analog-to-digital converter (ADC) voltage for I=V/R. The voltage across the heater can be determined by finding the voltage difference across the heater input pins or $V_{Heater} = V_{heaterInput1} - V_{HeaterInput2}$. R=V/I and the resistance can be calculated, and changed by adjusting the voltage across the device.

Figure 6A:
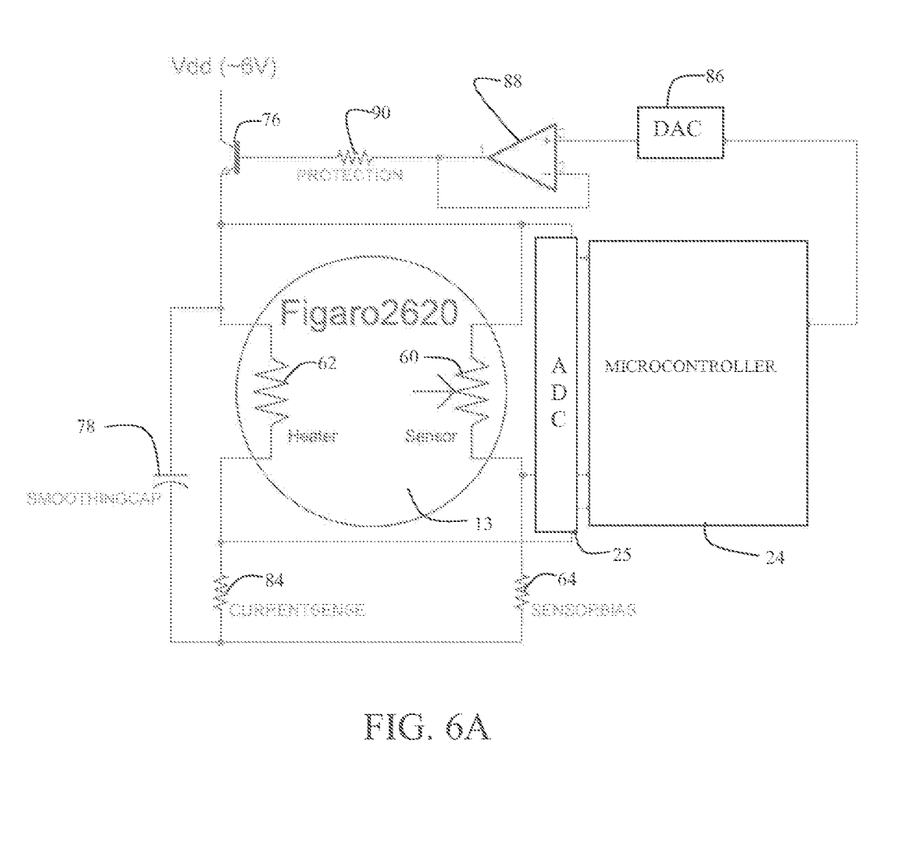
FIG. 6A is a schematic of a vapor sensor employing the heater element for temperature compensation; and, FIG. 6B is a schematic of a vapor sensor employing the heater element for temperature compensation with pulse width modulation control.

As seen in FIG. 6A, using analog control of control transistor 76 from the power supply, Vdd, a voltage value at the output of the control transistor 76 and a voltage value at the output of the internal heater 62 are provided to the microcontroller 24. As described, the microcontroller 24 calculates the resistance of the heater 62 with a known current sense resistor 84 and provides an output through a digital to analog (DAC) converter 86 to an operational amplifier 88 which provides gating for the control transistor 76 through a protection resistor 90 to control the power to the vapor sensor 13.

Figure 6B:
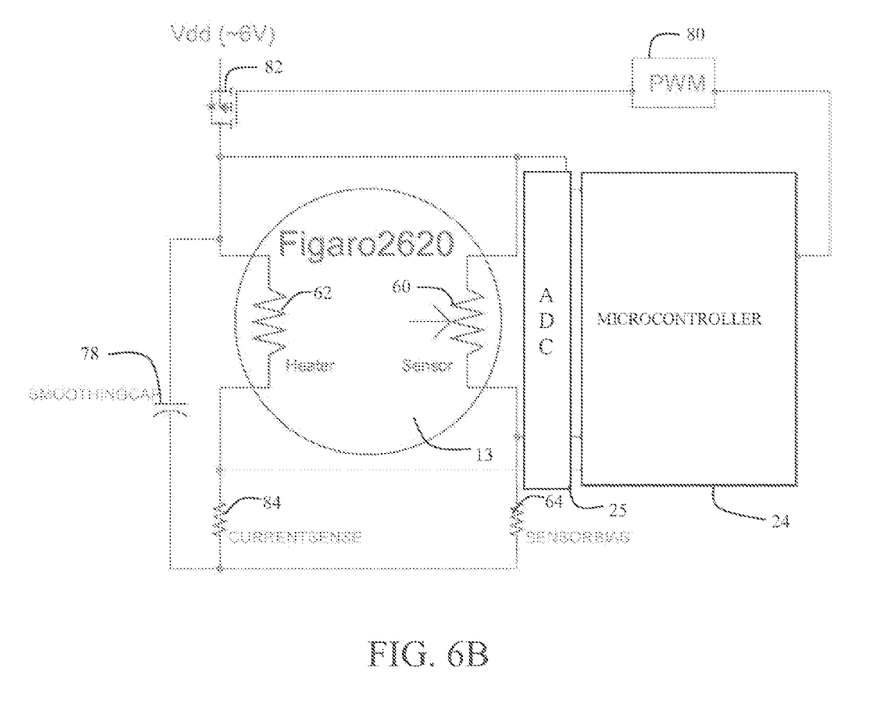

As described for the sensor element feedback circuit, the heater element feedback may also be employed digitally as shown in FIG. 6B. The calculated resistance output from the microcontroller 24 may be employed as a control signal through a PWM generator 80 which provides RMS averaging to a gating switch 82 between the power source, Vdd, and the vapor sensor 13.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. An alcohol detection system comprising:
a resistive vapor sensor having internal components of an alcohol vapor sensor element and a heating element, mountable in a vehicle for determining presence of alcohol based on ethanol content of vapor excreted from skin, said vapor sensor triggered for an initial reading by a touch sensor and triggered for a second reading at a predetermined time differential, one of the internal components, said alcohol vapor sensor element or said heating element, connected to automatically provide temperature compensation;
an ignition interlock in the vehicle;
a microcontroller connected to the internal component and providing feedback control to a heater in the resistive vapor sensor for temperature compensation and receiving data from the vapor sensor for comparison of the initial reading and the second reading, the microcontroller further connected to the ignition interlock and providing a signal to open the interlock to disable the vehicle upon a determination of differential of data from the vapor sensor at the initial reading and the second reading exceeding a predetermined value.

2. The alcohol detection system as defined in claim 1 further comprising an identity verification system for an operator touching the touch sensor, said identify verification system selected from the set of a fingerprint reader, said fingerprint reader connected to and providing data to the microcontroller or a camera providing image data to the microcontroller.

3. The alcohol detection system as defined in claim 2 wherein the identity verification system includes an operator detector.

4. The alcohol detection system as defined in claim 1 wherein said heating element internal to the resistive vapor sensor is connected to automatically provide temperature compensation.

5. The alcohol detection system as defined in claim 4 wherein the microcontroller receives a voltage differential across the internal heater and provides a responsive control output to an operational amplifier as a control input to a transistor intermediate a power source and the resistive vapor sensor.

6. The alcohol detection system as defined in claim 4 wherein the microcontroller receives a voltage differential across the internal heater and provides a responsive control output to a pulse width modulation circuit as a control input to a power source providing power to the resistive vapor sensor.

7. The alcohol detection system as defined in claim 4 wherein the microcontroller receives a voltage differential across the alcohol vapor sensor element and provides a responsive control output to an operational amplifier as a control input to a transistor intermediate a power source and the resistive vapor sensor.

8. The alcohol detection system as defined in claim 4 wherein the microcontroller receives a voltage differential across the alcohol vapor sensor element and provides a responsive control output to a pulse width modulation circuit as a control input to a power source providing power to the resistive vapor sensor.

9. The alcohol detection system as defined in claim 1 said alcohol vapor sensor element internal to the resistive vapor sensor is connected to automatically provide temperature compensation.

10. The alcohol detection system as defined in claim 1 further comprising a data logger connected to the microcontroller, said data logger receiving and storing data from the microcontroller including touch sensor data.

11. The alcohol detection system as defined in claim 1 further comprising a GPS locator connected to and providing location data to the microcontroller.

12. The alcohol detection system as defined in claim 1 further comprising a global system for modular communications transmitter/receiver connected to the microcontroller, whereby the touch sensor data may be transmitted to a remote facility by the microcontroller.

13. The alcohol detection system as defined in claim 1 wherein the touch sensor is a tin oxide Taguchi type sensor and the predetermined time differential is 6 seconds.

14. The alcohol detection system as defined in claim 1 further comprising operator indicators including a first LED connected to the microcontroller and illuminating upon activation by the microcontroller at a predetermined time for initiating an alcohol test, a second LED connected to the microcontroller and illuminating upon commencement of an alcohol test and remaining illuminated for the predetermined time differential and a third LED connected to the microcontroller and illuminating upon a failed alcohol detection test.

15. An alcohol detection system for installation in a vehicle comprising:
a resistive touch sensor and a fingerprint reader mounted in a detector case in a vehicle, said touch sensor for determining contact of a finger based on skin resistance and presence of alcohol based on ethanol content of vapor excreted from skin, said resistive touch sensor including a vapor sensor having a heater element and an alcohol vapor sensor element integral to said sensor, a selected one of said heater element and alcohol vapor sensor element monitored for temperature compensation, with power to said vapor sensor controlled by feedback from said selected one of said heater element and alcohol vapor sensor element, said vapor sensor triggered for an initial reading upon touch and triggered for a second reading at a predetermined time differential, a determination of differential of data from the vapor sensor at the initial reading and the second reading compared to a predetermined value, and said fingerprint reader for verifying the identity of an operator touching the resistive touch sensor;
an ignition interlock in the vehicle;
a microcontroller connected to and receiving data from the touch sensor and the fingerprint reader, the microcontroller further connected to the ignition interlock and providing a signal to open the interlock to disable the vehicle upon determination of the differential of data from the touch sensor exceeding a predetermined value;
operator indicators including a first LED connected to the microcontroller and illuminating upon activation by the microcontroller at a predetermined time for initiating an alcohol test, a second LED connected to the microcontroller and illuminating upon commencement of an alcohol test and remaining illuminated during a predetermined test period, and a third LED connected to the microcontroller and illuminating upon a failed alcohol detection test;

a location system incorporating a GPS locator connected to and providing location data to the microcontroller;

a data logger connected to the microcontroller, said data logger receiving and storing data from the microcontroller including touch sensor data, fingerprint reader data and location data; and, a global system for modular communications transmitter/receiver connected to the microcontroller, whereby the touch sensor data, identity data and location data may be transmitted to a remote facility by the microcontroller.

16. A method for disabling a vehicle with an alcohol detection system including a resistive touch sensor comprising:

initiating a microcontroller by powering an alcohol detection system on;

directing a data logger with the microcontroller to record a startup time;

activating an operator indicator with the microcontroller to notify an operator that a test is required at a predetermined time programmed into the microcontroller;

temperature correcting a vapor sensor having an alcohol vapor sensor element and a heater element using a selected one of the alcohol vapor sensor element or heater element;

reading vapor sensor data with the microcontroller when the operator places a finger on a touch sensor;

activating a second operator indicator with the microcontroller that the test is in process;

activating the elements of an identity verification system and location and anti-theft system with the microcontroller;

collecting data with the microcontroller from the vapor sensor at a predetermined time differential, identity verification system and a location and antitheft system;

if the operator removes his finger before testing is completed at the predetermined time interval, returning to the step of activating the operator indicator a requiring the operator to restart the test;

extinguishing the second operator indicator notifying the operator that the test is complete;

storing time/date information and data from the touch sensor, identity verification system and location and anti-theft system in a data logger;

if the test result shows impairment based on determination of a differential of data from the touch sensor at the predetermined time differential exceeding a predetermined value, notifying operator by illuminating a third operator indicator with the microprocessor to show test failure;

opening the ignition interlock under control of the microprocessor preventing operation of the vehicle; and, if no impairment is shown by the test, inactivating the microcontroller for a predetermined period until additional testing is required.

17. The method of claim 16 further comprising: transmitting data commanded by the microcontroller using a global system for modular communications transmitter/receiver with test result data, vehicle location and driver identification.

18. The method of claim 16 wherein the step of opening the ignition interlock further comprises illuminating a vehicle hazard flasher under control of the microprocessor.

19. The method of claim 16 wherein the step of activating the elements of an identity verification system includes activating a fingerprint reader with the microcontroller and activating a camera with the microcontroller for photographic images of the operator.

20. The method of claim 16 wherein the step of temperature correcting comprises providing feedback from the internal component to control power to the vapor sensor.

* * * * *